United States Patent [19]

Shroff et al.

[11] 4,264,505
[45] Apr. 28, 1981

[54] SUBSTITUTED BENZYLIDENE IMINES

[75] Inventors: James R. Shroff, Riverside, Conn.; Rohit Desai, Yonkers, N.Y.

[73] Assignee: USV Pharmaceutical Corporation, Tuckahoe, N.Y.

[21] Appl. No.: 107,020

[22] Filed: Dec. 26, 1979

Related U.S. Application Data

[63] Continuation-in-part of Ser. No. 914,405, Jun. 12, 1978, abandoned.

[51] Int. Cl.$^3$ .................. C07C 149/42; C07D 295/00
[52] U.S. Cl. .................. 260/326.5 S; 260/326.84; 260/453 RW; 546/232; 546/281; 424/267; 424/274; 424/299
[58] Field of Search ............... 260/453 RW, 326.84, 260/326.53; 546/232

[56] References Cited

U.S. PATENT DOCUMENTS 3,669,974   6/1972   Elpern et al. .................. 260/564 R Primary Examiner—Alton D. Rollins
Attorney, Agent, or Firm—Leon E. Tenenbaum

[57] ABSTRACT

Compounds of the formula

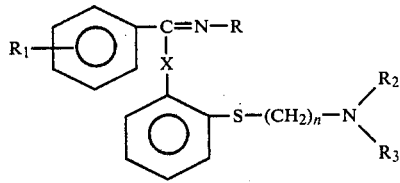

wherein
R is lower alkyl, phenyl, lower alkenyl, cycloalkyl and substituted phenyl;
$R_1$ is hydrogen, lower alkyl, lower alkenyl, lower alkoxy, amino, lower alkylamino, hydroxy, halo, nitro, mercapto, trifluoromethyl, lower alkylmercapto, and trifluoromethylmercapto;
$R_2$, $R_3$ are lower alkyl or taken together with N form a cyclic amine;
X is O or S, and
n is an integer from 2 to 4
are useful in treatment of arrhythmia.

8 Claims, No Drawings

SUBSTITUTED BENZYLIDENE IMINES

This application is a continuation-in-part of patent application Ser. No. 914,405, filed June 12, 1978, now abandoned.

This invention relates to new organic compounds having valuable pharmacological activity and to a process for the preparation of said compounds. In particular, the invention relates to derivatives of benzylidene imines of the formula

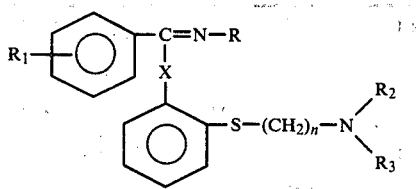

and their pharmaceutically acceptable, non-toxic acid addition salts,
wherein

R is lower alkyl, phenyl, lower alkenyl, cycloalkyl and substituted phenyl;

$R_1$ is hydrogen, lower alkyl, lower alkenyl, lower alkoxy, amino, lower alkylamino, hydroxy, halo, nitro, mercapto, trifluoromethyl, lower alkylmercapto, and trifluoromethylmercapto;

$R_2$, $R_3$ are lower alkyl and may be the same or different or taken together with N form a cyclic amine;

X is O or S, and n is an integer from 2 to 4.

The lower alkyl, lower alkoxy and lower alkenyl may be branched or straight chained and contain up to six (6) carbon atoms. The cycloalkyl groups contain from three (3) to seven (7) carbon atoms in the ring which may also carry a lower alkyl substituent.

The halo group may be fluoro, bromo, chloro or iodo.

The compounds of the present invention are prepared by the reaction of a benzimidoyl chloride of the formula

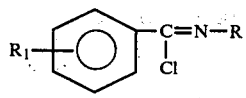

with an aminoalkylthiophenol, thiophenol or aniline of the formula

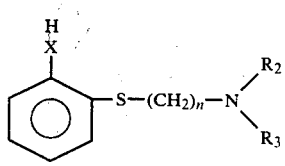

wherein R, $R_1$, $R_2$, $R_3$, X and n are the same as defined above.

The benzimidoyl chlorides were prepared by first preparing a benzamide from a corresponding benzoyl chloride and an amine under the standard Schotten-Baumann procedure and then converting this amide to the benzimidoyl chloride by treatment with thionyl chloride or phosphorus pentachloride according to the procedure in Organic Syntheses, Collective Volume 4, page 283.

The aminoalkylmercapto-anilines were prepared by the reaction of an amino alkyl halide with the sodium salt of o-thioaniline. The aniline could be readily converted to the corresponding phenol by the method described in Organic Syntheses, Collective Volume 3, page 130, or to the corresponding thiophenol by the method described in Organic Syntheses, Volume 27, page 81.

The hydrochloride salts were sometimes obtained directly. Such salts could be converted to the free bases from which the acid addition salts were prepared by treating the base in an inert solvent with the desired amount of acid to form the mono-, di- or triacidic salt. Suitable acids for preparing such salts include hydrochloric, hydrobromic, phosphoric, sulfuric, benzoic, mandelic, cinnamic, acetic, propionic, lactic, citric, tartaric, malic, malonic, succinic, maleic, and fumaric.

The invention will be more fully illustrated in the examples that follow. These examples are given by way of illustration and are not to be considered as limiting.

EXAMPLE 1

2-[β-(1-pyrrolidinyl)ethylthio]phenyl-N-phenylbenzimidate hydrochloride

A solution of 5.5 gms (0.025 mole) of 2-[β-(1-pyrrolidinyl)ethylthio]phenol and 5.3 gms (0.025 mole) of N-phenylbenzimidoyl chloride in 50 ml acetone was stirred at room temperature for a period of two hours. The desired product crystallized out. It was filtered, washed with acetone and dried at room temperature. Recrystallization from isopropanol yielded 6.0 gms (55%) of product, M.P. 167°–9° C.

EXAMPLE 2

2-[β-(1-pyrrolidinyl)ethylthio]phenyl-N-phenylbenzthioimidate hydrochloride

A solution of 5.3 gms (0.025 mole) of N-phenylbenzimidoyl chloride and 6.0 gms (0.025 mole) of crude 2-[β-(1-pyrrolidinyl)ethylthio]benzenethiol in 50 ml acetone was refluxed for a period of 8 hours. The solution was filtered and the filtrate concentrated to obtain an oily residue which was slurried in water and made basic with 2 N NaOH. The oily base was extracted with 50 ml ether, washed with water and dried over anhydrous MgSO₄. The dry ethereal solution was converted to the hydrochloride salt by addition of ethereal hydrogen chloride. The hydrochloride salt was triturated with water, filtered and recrystallized from acetonitrile to yield 3.5 gms (31%) of product, M.P. 170°–172° C.

Following the procedures in the previous examples, the compounds listed in Table I were prepared:

TABLE 1

| R | $R_1$ | X | n | $R_3$ | MP°C. | m |
|---|---|---|---|---|---|---|
| —CH₃ | H | NH | 3 | N(CH₃)₂ | 139–143 | 2 |

TABLE 1-continued
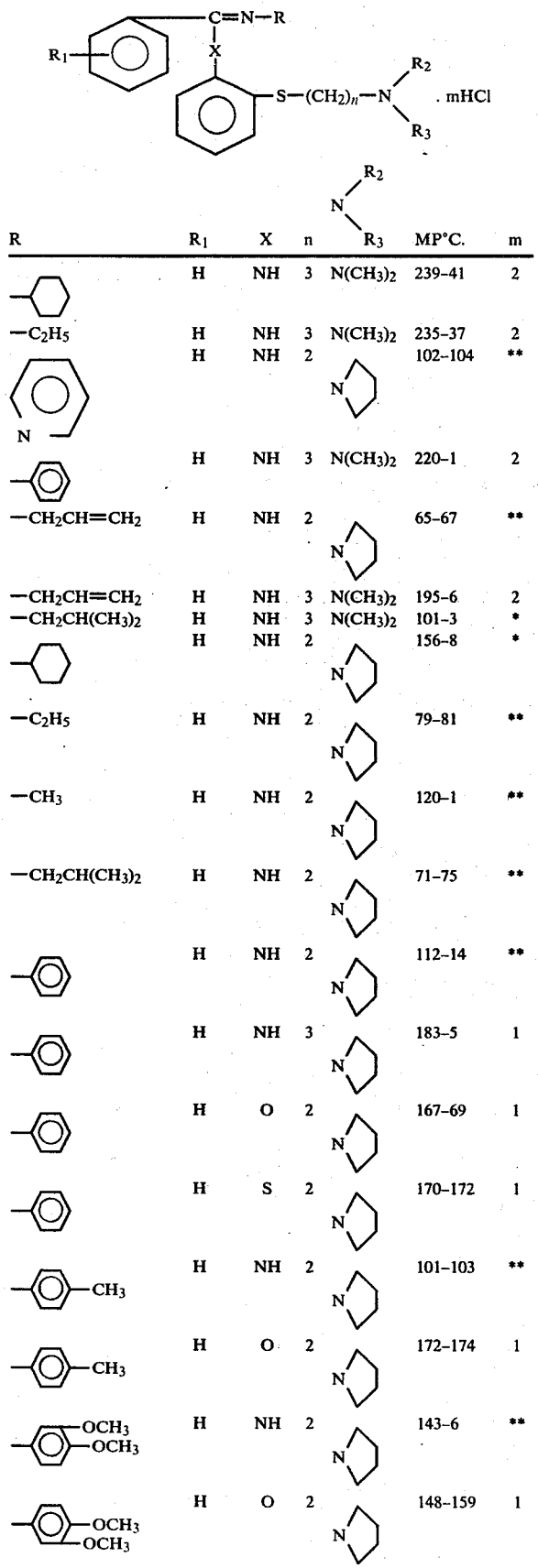
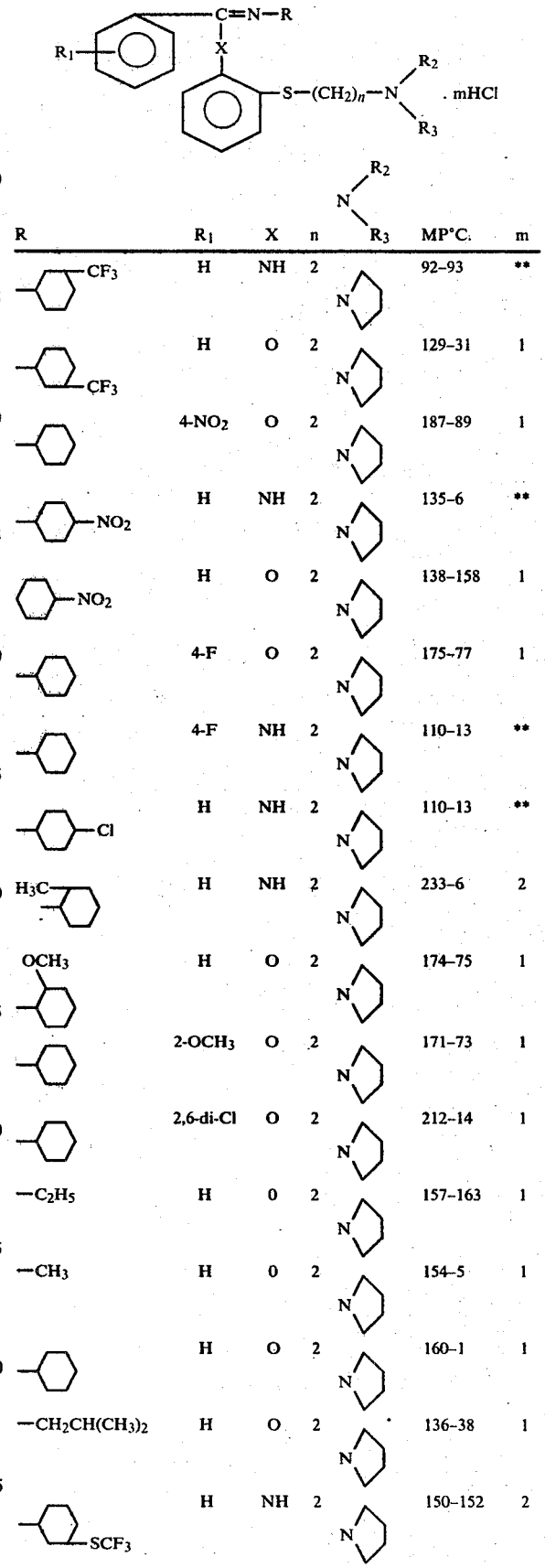

TABLE 1-continued

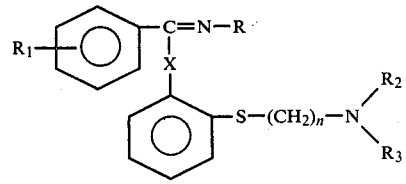

| R | R₁ | X | n | NR₂R₃  | MP °C. | m |
|---|---|---|---|---|---|---|
| —⟨○⟩—NH₂ | H | NH | 2 | pyrrolidino | 230–232 | 3 |
| —⟨○⟩—SCF₃ | H | O | 2 | pyrrolidino | 158–60 | 1 |
| —⟨○⟩ | H | O | 2 | N(CH₃)₂ | 171–72 | 1 |
| —CH₂CH=CH₂ | H | O | 2 | N(CH₃)₂ | — | ** |
| —CH₂CH=CH₂ | H | O | 2 | pyrrolidino | 159–161 | 1 |
| —⟨○⟩ | H | NH | 2 | N(C₃H₇)₂ | 135–38 | 2 |
| —⟨○⟩ | H | O | 2 | pyrrolidino | 235–36 | 1 |
| —CH₂CH=CH₂ | H | O | 2 | pyrrolidino | 142–144 | 1 |

** MP of free base
* Maleate Salt

The compounds of the present invention possess anti-arrhythmic activity which would make them useful in the treatment of auricular fibrillation and other heart conditions associated with arrhythmia. In in vitro screening for anti-arrhythmic activity using isolated atria from guinea pigs the compounds of the present invention exhibited an ED₅₀ at a concentration of about 1.57 mg/l which is considerably lower than the activity exhibited by known anti-arrhythmic compounds (e.g., quinidine sulfate 14.1, propanolol hydrochloride 3.9, lidocaine hydrochloride 5.0, and procainamide hydrochloride 150.0).

In in vivo screening the compounds of the present invention exhibited an ED₅₀ of about 15 mg/kg in providing protection against chloroform-induced ventricular arrhythmia in mice. This information will enable a physician to select the proper dose for his patients depending upon age, weight, sex and other considerations.

The compound of Examples 1 and 2 and the compound where R₁ is allyl, R₁ is H, X is O, n is 2 and N(R₂)(R₃) is pyrrolidino are the most active.

The compounds may be mixed with solid or liquid pharmaceutical carriers and formulated into tablets, powders or capsules for oral administration or dissolved in suitable solvents for either oral or parenteral administration.

We claim:

1. A compound of the formula $$R_1-\text{C}_6\text{H}_4-\underset{X}{\overset{}{\text{C}}}=\text{N}-\text{R}$$
with ortho phenyl-S-(CH₂)ₙ-NR₂R₃ wherein
R is lower alkyl, lower alkenyl, cycloalkyl, phenyl or phenyl substituted with methyl, trifluoromethyl, trifluoromethylmercapto, nitro or methoxy; the cycloalkyl group having from 3 to 7 carbon atoms;
R₁ is hydrogen, lower alkoxy, halo or nitro;
R₂ and R₃ are lower alkyl and may be the same or different or taken together with the N to which they are attached are piperidino or pyrrolidino;
X is O or S, and
n is an integer from 2 to 4, and its pharmaceutically acceptable, nontoxic acid addition salts.

2. A compound according to claim 1 wherein $$-N\begin{matrix}R_2\\R_3\end{matrix}$$

is pyrrolidino.

3. A compound according to claim 2 wherein R₁ is hydrogen.

4. A compound according to claim 3 wherein R is cyclohexyl.

5. A compound according to claim 2 wherein R is phenyl.

6. A compound according to claim 5 wherein X is oxygen.

7. A compound according to claim 5 wherein X is sulfur.

8. A compound according to claim 3 wherein X is oxygen and R is allyl.

* * * * *